United States Patent [19]

Hodges et al.

[11] Patent Number: 5,445,818
[45] Date of Patent: Aug. 29, 1995

[54] SYNTHETIC PSEUDOMONAS AERUGINOSA PILIN PEPTIDE VACCINE AND METHOD OF USE

[75] Inventors: Robert S. Hodges; William Paranchych; Kok K. Lee; Sastry A. Parimi, all of Edmonton; Randall T. Irvin, Mississauga; Peter C. Doig, Toronto, all of Canada

[73] Assignee: The Governors of the University of Alberta, Alberta, Canada

[21] Appl. No.: 927,797

[22] Filed: Aug. 10, 1992

Related U.S. Application Data

[63] Continuation of Ser. No. 344,565, Apr. 28, 1989, abandoned.

[51] Int. Cl.$^6$ ............... A61K 39/02; A61K 39/38; A61K 38/10; C07K 1/00
[52] U.S. Cl. ............... 424/184.1; 424/185.1; 424/260.1; 530/300; 530/327; 530/350
[58] Field of Search ........... 424/92, 88, 184.1, 185.1, 424/260.1; 530/300, 350, 326, 327; 540/88, 42, 350, 300

[56] References Cited

U.S. PATENT DOCUMENTS

| | | | |
|---|---|---|---|
| 4,443,549 | 4/1984 | Sadowski | 436/548 |
| 4,702,911 | 10/1986 | McMichael | 424/92 |

FOREIGN PATENT DOCUMENTS

| | | | |
|---|---|---|---|
| 48422 | 3/1982 | European Pat. Off. | A61K 39/104 |
| 85/00565 | 10/1985 | WIPO | C07C 103/52 |

OTHER PUBLICATIONS

Pier et al, Infect & Immunity 60: 4768–4776, 1992, Murine Model of Chronic Mucosal Colonization by PS. Hernginosa.
Sastry et al Journal of Bact 164: 571–577 1985.
Pasloske et al Journal of Bact 170: 3738–3741 1988.
Paranchych et al Clinical & Invest Med. 9: 113–118 1986.
Lee et al Inf & Imn. Feb. 1989 57:520–526.
Tramont et al The Pathogenic Neisseriae, pp. 316–321.
Watts et al I & I 42: 113–121 1983.
Paranchych et al. Antibiol Chem. 36: 49–57 1985.
Parker Biochemistry 25: 5425–5432 1986.
Stryndaka et al J of Virol 62: 3474–3483 1988.
Watts el Infect & Imm vol. 42 Oct. 1983 pp. 113–121.
Paranchych et antibiot Chemother vol. 36 1985 pp. 49–57.
Parker Biochemistry vol. 25 Sep. 23 1986 pp. 5425–5432).
H. Marcus et al., Infection and Immunity, vol. 47, No. 3, pp. 723–729 (1985).
R. Ramphal et al., Infection and Immunity, vol. 44, pp. 38–40 (1984).
R. Ramphal et al., Infection and Immunity, vol. 47, pp. 1–4 (1985).
D. Woods et al., Infection and Immunity, vol. 29, pp. 1146–1151 (1980).

(List continued on next page.)

*Primary Examiner*—Hazel F. Sidberry
*Attorney, Agent, or Firm*—Peter J. Dehlinger; Carol A. Stratford

[57] ABSTRACT

Treatment and diagnosis of *P. aeruginosa* infection or colonization is achieved in accordance with this invention by the discovery of a polypeptide which is smaller than the naturally occurring *P. aeruginosa* pillin protein. The pure polypeptide comprises at least one amino acid residue sequence containing about twelve amino acid residues and up to about twenty amino acid residues that define a sequence capable of immunologically mimicking an antigenic determinant cite of *P. aeruginosa* pilin. This amino acid residue sequence can repeat as a unit one or more times in the same polypeptide molecule. More than one of such repeating units and more than one repeating unit of the same type can be present in a single polypeptide molecule. The polypeptides act an antigens or immunogens and antibodies may be raised to the immunogens and a vaccine prepared suitable for the prevention of *P. aeruginosa* infection.

2 Claims, 8 Drawing Sheets

OTHER PUBLICATIONS

E. Beachey, J. Infect. Dis., vol. 143, No. 3, pp. 325–345 (1981).

W. Paranchych et al., Antibiot. Chemother., vol. 36, pp. 49–57 (1985).

P. Doig et al., Infection and Immunity, vol. 56, No. 6, pp. 1641–1646.

P. Doig et al., Infection and Immunity, vol. 55, No. 6, pp. 1517–1522 (1987).

D. McEachran et al., Can. J. Microbiol., vol. 31, pp. 563–569 (1985).

D. McEachran et al., J. Microbiol. Meth., vol. 5, pp. 99–111 (1986).

Pasloske, B. L., et al., Journal of Bacteriol. 170:3738–3741 (1988).

Stryndaka, N. C. J., et al., Journal of Virol. 62:3474–3483 (1988).

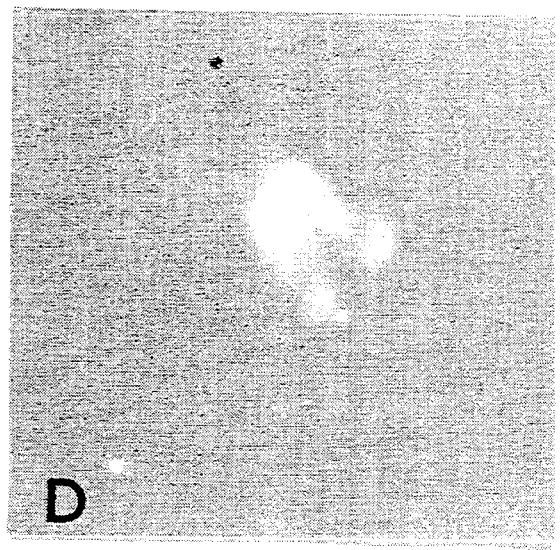
Fig. 5D
Fig. 5E
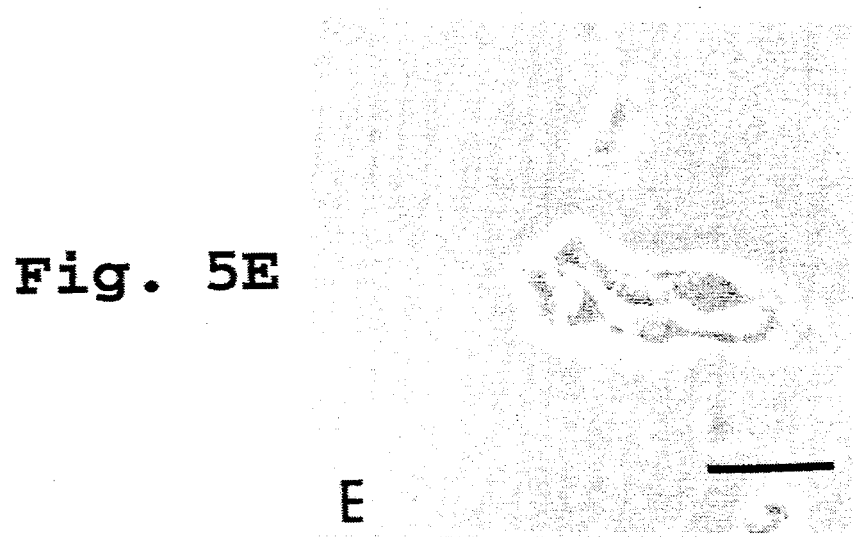
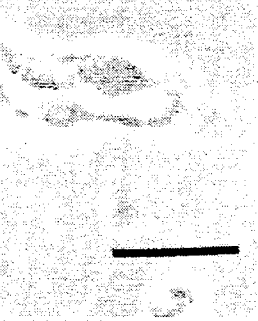
Fig. 5F

SYNTHETIC PSEUDOMONAS AERUGINOSA PILIN PEPTIDE VACCINE AND METHOD OF USE

This application is a continuation of application Ser. No. 344,565, filed Apr. 28, 1989 now abandoned.

FIELD OF THE INVENTION

This invention relates to antigens, immunogens and to vaccines utilizing such immunogens. More particularly, this invention relates to polypeptide antigens or immunogens, antibodies raised by such immunogens, and a vaccine suitable for the prevention of *P. aeruginosa* infection or colonization.

BACKGROUND OF THE INVENTION

During the past two decades, *Pseudomonas aeruginosa* has been recognized as a pathogen which causes between 10% and 20% of infections in most hospitals. Pseudomonas infection is especially prevalent among patients with burn wounds, cystic fibrosis, acute leukemia, organ transplants, and intravenous-drug addiction. *P. aeruginosa* is a common nosocomial contaminant, and epidemics have been traced to many items in the hospital environment. Patients who are hospitalized for extended periods are frequently affected by this organism and are at increased risk of developing infection. The most serious infections include malignant-external otitis, endophthalmitis, endoconditis, meningitis, pneumonia, and septicemia. The likelihood of recovery from Pseudomonas infection is related to the severity of the patient's underlying disease process. The reported mortality for *P. aeruginosa* pneumonia is as high as 50-80%. Even with the development of newer antibiotics, resistance remains a problem necessitating combined antibiotic treatment for severe *P. aeruginosa* infections.

Alternative therapy for the management of severe *P. aeruginosa* infections have been evaluated for many years. Immunotherapy has been the alternative most extensively explored. In this area, attention has focussed on the virulence factors. As with most bacterial pathogens, virulence of *Pseudomonas aeruginosa* is multifactorial and is the product of many interacting variables, involving both the bacterium and the host.

Evidence suggests that the initial event in infection is the adherence of microorganisms to epithelial cells of mucosal surfaces [E.H. Blackey, J. Infect. Dis., 143:325–345 (1981)]. Organisms that are unable to adhere to mucosal surfaces fail to colonize because they are removed by the secretions that bathe the mucosal surfaces. The adherence process is dependent upon the specific recognition between bacteria and epithelial cells. For a number of gram-negative bacteria, including *P. aeruginosa*, attention has been directed to surface appendages as mediations of adherence. These surface appendages are termed 'adhesins', and the distribution of specific receptors for adhesins determines many of the tissue tropisms noted for bacteria. In the case of *P. aeruginosa*, polar pili present on the surface of the organism have been shown to mediate adherence to buccal epithelial cells. The evidence for this is as follows: (1) nonpiliated strains do not adhere to epithelial cells; (2) protease treatment of *P. aeruginosa* drastically reduces the ability of these organisms to adhere to epithelial cells; (3) preincubation of epithelial cells with purified pili significantly decreases the adherence of intact organisms, and (4) antibody to purified pili prevents the adherence of organisms to buccal epithelial cells.

Although *P. aeruginosa* pili are antigenically heterogeneous in different clinical isolates, there is evidence that a portion of the pilus is conserved [see Paranchych et al., Antibiotics Chemother. 36:49–57 (1985)]. As this common domain is important in binding to epithelial cells [see Doig et al., Infection and Immun., 56: 1641–1646 (1988)], it is useful in the production of a broadly effective *P. aeruginosa* pili vaccine.

The surface of many gram-negative bacteria, e.g., *E. coli, P. aeruginosa M. bovis, N. gonorrhea,* are covered with filamentous structures called pili or fimbriae. Pili are composed primarily of protein (pilin) and have been found to act as antigenic determinants when injected into test animals. Certain pili, including PAO, PAK, CD4, as they are commonly referred to, and others, mediate the colonization of *P. aeruginosa* in humans. Some bacterial cells lacking these pili, either through mutation or loss of the plasmid carrying the pilus gene, are incapable of colonizing mucosa. Apparently, the pili on the surface of the bacterium adhere to the lining of the throat and trachea through specific interactions with epithelial cell receptors. *P. aeruginosa* can utilize both pili and alginate (the principle component of the *P. aeruginosa* capsule) as adhesins to mediate attachment to human respiratory epithelial cells [see Doig et al., Infection and Immun., 55: 1517–1522 (1987); Doig et al., Infection and Immun., 56: 1641–1646 (1988); Marcus et al., *Infection and Immun.,* 47:723–729 (1985); Ramphal et al., *Infection and Immun.* 44: 38–40 (1984); Ramphal et al., *Infection and Immun.,* 47:1–4 (1985); Woods et al., *Infection and Immun.,* 29: 1146–1151 (1980).

Equilibrium analysis of *P. aeruginosa* binding to human respiratory epithelial cells indicates that the Pseudomonas pilus adhesin has a considerably higher apparent affinity or binding constant (Ka) than does the alginate adhesin [McEachran et al., *Can. J. Microbiol.* 31:563–569 (1985), McEachran et al., *J. Microbiol. Meth.,* 5: 99–111 (1986); Doig et al., *Infection and Immun.,* 55: 1517–1522 (1987)].

These observations suggest that the pilus adhesin is likely the dominant Pseudomonas adhesin in the initiation of an infection. Adhesin-mediated anchorage is a prerequisite for the induction of disease by *P. aeruginosa.*

Anything which would biologically interfere with this adhesion should be effective in blocking infection. Such a technique has been investigated by monoclonal antibody treatment of bacterial adhesion and has been reported in the patent literature, e.g., U.S. Pat. No. 4,443,549 and U.S. Pat. No. 4,702,911 and published U.S. PCT application Ser. No. PCT/US85/00565. It is important to note that bacterial adhesins are unique so that this technique is not predictable with various other bacteria.

SUMMARY OF THE INVENTION

According to an aspect of the invention, a polypeptide is provided that is smaller than a naturally-occurring *P. aeruginosa* pilin protein, and the pharmaceutically acceptable salts thereof; that are capable of immunologically mimicking a conserved antigenic determinant site within a semi-variable region of the carboxy-terminal half of the *P. aeruginosa* pilin and thus are capable of being an antigen, or an immunogen, operable in blocking a *P. aeruginosa* infection. Additionally, the present invention provides a vaccine that contains such an immunogen as well as a method of immunization against a *P. aeruginosa* infection. This invention further contemplates a diagnostic assay utilizing a polypeptide of this invention and/or a receptor such as an antibody elicited by such a polypeptide.

According to an aspect of the invention, the pure homogeneous polypeptide comprises at least one amino acid residue sequence, containing about 12 amino acid residues and up to about 20 amino acid residues, that defines a sequence capable of immunologically mimicking an antigenic determinant site of a *P. aeruginosa* pilin. This amino acid residue sequence can repeat as a unit one or more times in the same poly-peptide molecule. More than one type of such repeating unit, and more than one repeating unit of the same type, can be present in a single polypeptide molecule that embodies the present invention.

Such a polypeptide can be made as a protein synthesized by genetic engineering techniques or it can be built-up from individual amino acid residues, or amino acid residue blocks.

According to a preferred aspect of the invention, pure homogeneous polypeptides embodying this invention can be defined as including the amino acid residue sequence, taken from left to right and in the direction from the amino-terminus to the carboxy-terminus, of the formula:

$$-X_1-X_2-X_3-X_4-X_5-X_6-X_7-X_8-X_9-X_{10}-X_{11}-X_{12}-X_{13}-X_{14}-X_{15}-X_{16}-X_{17}-X_{18}-X_{19}-X_{20}-$$

wherein the X designates an amino acid residue or a blank. If a blank occurs between residues $X_n$ and $X_{n+2}$, where n=1 to 18, then Xn is connected to $X_{n+2}$ through an amide bond (-CONH-). This amide bond results from the condensation of the α-carboxy-terminus of residue $X_n$ with the α-amino-terminus of residue $X_{n+2}$.

In the above formula:

$X_1$ is the amino acid residue Cysteine (C);

$X_2$ is an amino acid residue from the group Glycine (G), Lysine (K), Serine (S) or is a blank;

$X_3$ is an amino acid residue from the group Alanine (A) or Isoleucine (I) or is a blank;

$X_4$ is an amino acid residue from the group Serine (S) or Threonine (T) or is a blank;

$X_5$ is an amino acid residue from the group Glycine (G), Lysine (K), Serine (S) or is a blank;

$X_6$ is an amino acid residue from the group Serine (S) or Threonine (T);

$X_7$ is an amino acid residue from the group Aspartic acid (D), Leucine (L), Asparagine (N), Proline (P) or is a blank;

$X_8$ is an amino acid from the group Alanine (A), Leucine (L), Valine (V) or is a blank;

$X_9$ is the amino acid Threonine (T) or is a blank;

$X_{10}$ is an amino acid from the group Alaninc (A), Asparagine (N), Glutamine (Q) or is a blank;

$X_{11}$ is an amlno acid residue from the group Glycine (G), Tryptophan (N) or is a blank;

$X_{12}$ is an amino acid residue from the group Aspartic acid (D), Glutamic acid (E), Lysine (K);

$X_{13}$ is an amino acid residue from the group Alanine (A), Glutamic acid (E), Asparagine (N), Proline (P);

$X_{14}$ is an amino acid residue from the group Lysine (K), Methionine (M), Asparagine (N), Glutamine (Q);

$X_{15}$ is an amino acid residue from the group Phenylalanine (F), Tyrosine (Y);

$X_{16}$ is an amino acid residue from the group Alanine (A), Isoleucine (I), Leucine (L), Arginine (R), Threonine (T);

$X_{17}$ is the amino acid residue Proline (P);

$X_{18}$ is an amino acid residue from the group Alanine (A), Lysine (K), Asparagine (N), Serine (S);

$X_{19}$ is an amino acid residue from the group Glycine (G), Asparagine (N), Threonine (T);

$X_{20}$ is the amino acid Cysteine (C).

Particularly preferred amino acid residue sequences within the above groupings taken from left to right, and in the direction from the amino-terminus to the carboxy-terminus, are:

```
C T S D Q D E Q F I   P K G C
C K S T Q D P M F T   P K G C
C T S T Q E E M F T   P K G C
C T S N A D N K Y L   P K T C
C A T T V D A K F R   P N G C
C K I T K T P T A W K P N Y A P A N C
C G I T G S P T N W K A N Y A P A N C
C S I S S T L L T G K P N Y A P S N C
```

The description of the synthetic peptide of this patent does not represent a previously published sequence but is a composite of the critical residues involved in binding to buccal and tracheal epithelial cell surface receptors. Several sequences have been published and are subsets of this composite sequence.

BRIEF DESCRIPTION OF THE DRAWINGS

Preferred embodiments of the invention are discussed with respect to the following Examples in which:

FIG. 5a-5f show micrographs A, B, C, D, E, and F of indirect immunofluorescent localization of binding of synthetic peptides to human ciliated TECs.

DETAILED DESCRIPTION OF THE PREFERRED EMBODIMENTS

Figure 1:
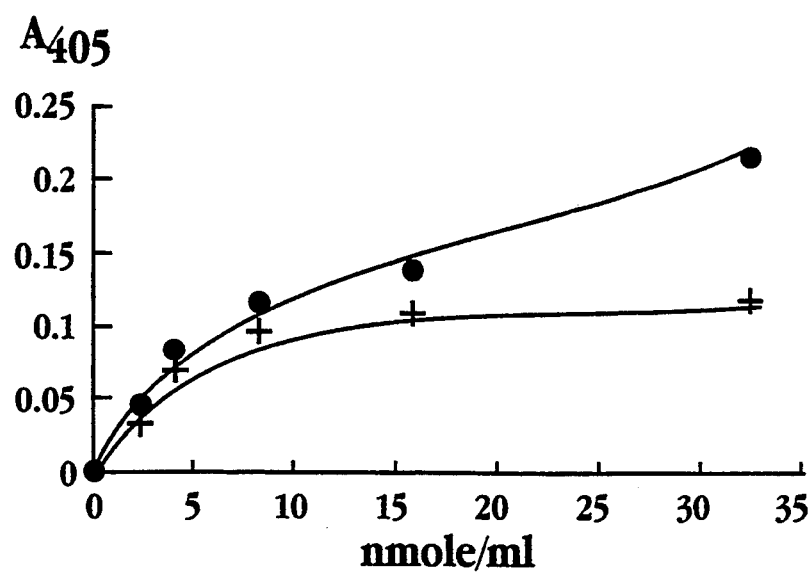
FIG. 1 is a graph showing the binding of synthetic peptide Ac17red and Ac17ox to human BECs.

Polypeptides of the present invention are smaller than the naturally-occurring *Pseudomonas aeruginosa* pilin protein and include an amino acid residue sequence of about 12 to about 20 amino acid residues, preferably 12 to 20 amino acid residues, that immunologically mimic a conserved antigenic determinant site in the region of the carboxy-terminal half of *P. aeruginosa* pilin protein. As such, the present polypeptides are useful by themselves, or as pharmaceutically acceptable salts, as the active constituent in a vaccine, as an inoculum, or in a diagnostic assay. The polypeptides of this invention are prepared by a variety of synthetic techniques as will be described. Such synthetic production of the subject polypeptides result in pure materials; i.e., homogeneous peptide sequences which are substantially free of at least any foreign biological materials.

The term "antigenic determinant" as used herein, designates the structural component of a molecule that is responsible for specific interaction with corresponding antibody (immunoglobulin) molecules elicited by the same or related antigen. Antigenic determinants in the present polypeptides comprise chemically active surface groupings of amino acid residues.

The term "antigen" as used herein, means an entity that is bound by an antibody.

The term "immunogen", as used herein, describes an entity that induces antibody production in the host animal. In some instances the antigen and the immunogen are the same entity, while in other instances the two entities are different.

The phrase "immunologically mimicks" is used herein to mean that an immunogenic polypeptide of this invention is not a natural protein or a cleaved fragment of a natural protein, but a manufactured polypeptide, as by solid phase synthesis or genetic engineering techniques, which polypeptide induces production of antibodies that bind to the inducing polypeptide and also to a corresponding pilin or pilin polypeptide portion.

All amino acid residues identified herein are in the natural or L-configuration unless otherwise specified. In keeping with standard peptide nomenclature, abbreviations for amino acid residues that have been used herein are as follows:

| Symbol | | |
|---|---|---|
| 1 Letter | 3 Letter | Amino Acid |
| Y | TYR | -L-tyrosine |
| G | GLY | -glycine |
| F | PHE | -L-phenylalanine |
| M | MET | -L-methionine |
| A | ALA | -L-alanine |
| S | SER | -L-serine |
| I | ILE | -L-isoleucine |
| L | LEU | -L-leucine |
| T | THR | -L-threonine |
| V | VAL | -L-valine |
| P | PRO | -L-proline |
| K | LYS | -L-lysine |
| N | ASN | -L-asparagine |
| H | HIS | -L-histidine |
| Q | GLN | -L-glutamine |
| E | GLU | -L-glutamic acid |
| W | TRP | -L-tryptophan |
| R | ARG | -L-arginine |
| D | ASP | -L-aspartic acid |
| C | CYS | -L-cysteine |

The term "pharmaceutically acceptable salts", as used herein, refers to the non-toxic salts, such as, alkali metal, alkaline earth metal and ammonium salts commonly used in the pharmaceutical industry including the sodium, potassium, lithium, calcium, magnesium, and ammonium salts and the like which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laureate, borate, benzoate, lactate, phosphate, tosylate, citrate, maleate, fumarate, succinate, tartrate and the like. The polypeptides meeting the foregoing conditions elicit antibodies in a mammalian host and are believed to immunologically mimic a desired antigenic determinant site within a region of the carboxy-terminal half of the pilin protein.

One or more amino acid residue sequences meeting the foregoing conditions can be present as repeating units. Additionally, polypeptides containing one or more such amino acid residue sequences can be formed into relatively larger synthetic moieties by joining the individual polypeptides head-to-tail.

These polypeptides can be characterized as those including the amino acid sequences taken from left to right in the direction from the amino-terminus to the carboxy-terminus, of the formula:

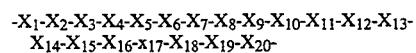

wherein the X designates an amino acid residue or a blank. If a blank occurs between residues $X_n$ and $X_{n+2}$, where n=1 to 18, then $X_n$ is connected to $X_{n+2}$ through an amide bond (—CONH—). This amide bond results from the condensation of the α-carboxy-terminus of residue $X_n$ with the α-amino terminus of residue $X_{n+2}$.

Additionally, $X_1$ is the amino acid residue Cysteine (C);

$X_2$ is an amino acid residue from the group Glycine (G), Lysine (K), Serine (S) or is a blank;

$X_3$ is an amino acid residue from the group Alanine (A) or Isoleucine (I) or is a blank;

$X_4$ is an amino acid residue from the group Serine (S) or Threonine (T) or is a blank;

$X_5$ is an amino acid residue from the group Glycine (G), Lysine (K), Serine (S) or is a blank;

$X_6$ is an amino acid residue from the group Serine (S) or Threonine (T);

$X_7$ is an amino acid residue from the group Aspartic acid (D), Leucine (L), Asparagine (N), Proline (P) or is a blank;

$X_8$ is an amino acid from the group Alanine (A), Leucine (L), Valine (V) or is a blank;

$X_9$ is an amino acid from the group Threonine (T) or is a blank;

$X_{10}$ is an amino acid from the group Alanine (A), Asparagine (N), Glutamine (Q) or is a blank;

$X_{11}$ is an amino acid residue from the group Glycine (G), Tryptophan (N) or is a blank;

$X_{12}$ is an amino acid residue from the group Aspartic acid (D), Glutamic acid (E), Lysine (K);

$X_{13}$ is an amino acid residue from the group Alanine (A), Glutamic acid (E), Asparagine (N), Proline (P);

$X_{14}$ is an amino acid residue from the group Lysine (K), Methionine (M), Asparagine (N), Glutamine (Q);

$X_{15}$ is an amino acid from the group Phenylalanine (F), Tyrosine (Y);

$X_{16}$ is an amino acid residue from the group Alanine (A), Isoleucine (I), Leucine (L), Arginine (R), Threonine (T);

$X_{17}$ is the amino acid residue Proline (P);

$X_{18}$ is an amino acid residue from the group Alanine (A), Lysine (K), Asparagine (N), Serine (S).

$X_{19}$ is an amino acid residue from the group Glycine (G), Asparagine (N), Threonine (T).

$X_{20}$ is the amino acid Cysteine (C).

Particularly preferred amino acid residue sequences within the above groupings taken from left to right, and in the direction from the amino-terminus to the carboxy-terminus, are:

```
C T S D Q D E Q F I   P K G C
C K S T Q D P M F T   P K G C
C T S T Q E E M F T   P K G C
C T S N A D N K Y L   P K T C
C A T T V D A K F R   P N G C
C K I T K T P T A W K P N Y A P A N C
C G I T G S P T N W K A N Y A P A N C
C S I S S T L L T G K P N Y A P S N C
``` which sequences have been found to be located in the region of the carboxy-terminus half of pilin proteins from eight different strains of *P. aeruginosa* as described by Pasloske et al., *J. of Bacteriology*, 170: 3738–3741 (1988).

Particularly preferred structures for the sequences described here are those in which these sequences contain intramolecular disulfide bonds. These disulfide bonds occur through oxidative coupling of the sulphur atoms of the two Cysteine (c) residues contained in each sequence.

In a typical laboratory preparation, 10 milligrams of the di-CYS-polypeptide (containing amino- and carboxy-terminal cysteine residues in unoxidized form) are dissolved in 250 milliliters of 0.1 molar ammonium bicarbonate buffer having a pH value of about 8. The dissolved di-CYS-polypeptide is then air oxidized by stirring the resulting solution gently for a period of about 18 hours, or until there is no detectable free mercaptan by the Ellman test. [See, Ellman, Arch. Biochem. Biophys. 82:70–77 (1959)]. The cyclized peptide so prepared is then typically isolated by freeze drying, redissolution and chromatographic purification.

These preferred sequences have been found to be conserved within the region of the carboxy-terminal half of pilin proteins from eight different strains of *P. aeruginosa* as described by Pasloske et al., *J. Bacteriology* 170:3738–3741 (1988) as well as antigenically related variants thereof as defined herein below.

More than one of the foregoing sequences can be present in the same polypeptide, usually spaced from one another by a chain of other amino acid residues or other suitable linking group.

Biochemical evidence from immunoassay and from analogy with conserved protein-protein interaction in solved X-ray crystallographic structures with differing sequences such as in the dimer contacts of oligomeric enzymes, indicates that the conservation of protein-protein recognition does not require a strict conservation of sequence, for relatedness. While single amino acid residue changes may affect such recognition to a wide degree depending upon the nature of the substitution, in general terms, the relatedness of two differing amino acid sequences with respect to protein-protein (and antigenic and/or immunogenic) recognition can be expressed in terms of seven basic amino acid parameters:

(1) hydrophobicity;
(2) polarity;
(3) size of side chain;
(4) charge;
(5) preference for turned secondary structure;
(6) preference for beta strand secondary structure; and
(7) preference for helical secondary structure.

To define the degree of sequence identity relevant to antigenic and/or immunogenic recognition, and thus antigenically related variants, the following classification using empirical similarities between amino acid residues can be used. This classification is based on an arrangement of amino acid residues which reveals exchange groups. Amino acids within such a group exchange preferentially with each other. Therefore, they resemble each other most with respect to their overall impact on protein structures. These empirical similarities are outlined in "Principles of Protein Structure" Charles R Cauton, Editor, Springer-Verlag, New York, Inc. 1979, page 14 and are as follows:

| Exchange Group | Description |
| --- | --- |
| 1 | The aromatics Phe (F), Tyr (Y) and Tryptophan (W); |
| 2 | The positively charged residues Lys (K), Arg (R) and His (H); |
| 3 | The large aliphatic nonpolar residues Val (V), Leu (L), Ile (I), Met (M) and Cys (C); |
| 4 | The small residues Ser (S), Thr (T), Asp (D), Asn (N), Gly (G), Ala (A), Glu (E), Gln (Q) and Pro (P). |

For the purpose of this invention a related peptide is defined in the following way:

As any peptide containing a Cysteine residue (C) at position $X_1$ followed by, an amino acid residue from groups 2 or 4 in position $X_2$ or a blank.

an amino acid residue from groups 3 or 4 in position $X_3$ or a blank.

an amino acid residue from group 4 in position $X_4$ or a blank.

an amino acid residue from groups 2 or 4 in position $X_5$ or a blank.

an amino acid residue from group 4 in position $X_6$ or a blank.

an amlno acid residue from groups 3 or 4 in position $X_7$ or a blank.

an amino acid residue from groups 3 or 4 in position $X_8$ or a blank.

an amino acid residue from group 4 in position $X_9$ or a blank.

an amino acid residue from group 4 in position $X_{10}$ or a blank.

an amino acid residue from groups 1 or 4 in position $X_{11}$ or a blank.

an amino acid residue from groups 2 or 4 in position $X_{12}$.

an amino acid residue from group 4 in position $X_{13}$.

an amino acid residue from groups 2, 3 or 4 in position $X_{14}$.

an amino acid residue from group 1 in position $X_{15}$.

an amlno acid residue from groups 2, 3 or 4 in position $X_{16}$.

an amino acid residue from group 4 in position $X_{17}$.

an amino acid residue from groups 2 or 4 in position $X_{18}$.

an amino acid residue from group 4 in position $X_{19}$.

and containing a Cysteine residue (c) at position $X_{20}$.

The peptides, according to this invention and used herein, are preferably coupled to higher molecular weight compounds. For example, proteins such as keyhole limpet hemocyanin (KLH) or bovine serum albumin (BSA) or toxoid proteins can be used in the following method.

Peptide Conjugation to Protein Carriers

The peptides were conjugated to keyhole limpet hemocyanin (KLH) or bovine serum albumin BSA via a linker consisting of a [$^{14}$C] glycine and a benzophenone cross-linking group (benzoyl benzoic acid), which was added to the peptide during synthesis while the peptide was still on a solid matrix. The hapten was first dissolved in 10–20 μl water in a test tube. The protein carriers (10 mg/100 μl) were then added and mixed. Covalent attachment of the peptide to the carrier occurs following activation of the benzoylbenzoyl group by UV irradiation at 4° C. for an hour in a RPR 208 preparative reactor equipped with RPR 3500 A lamps. Unconjugated hapten were removed by successive dialysis against 8M urea, 100 mM and 25 mM ammonium bicarbonate. The product was freeze-dried and the peptide incorporation determined by measuring the radioactivity incorporated per mole carrier. Peptide/protein ratios of about 4:1 and 10:1 were obtained for the oxidized and reduced peptides, respectively.

A mixture of the foregoing polypeptides, including those having antigenically-related regions as defined herein above, can also be used to make up a vaccine against or a diagnostic assay for a *P. aeruginosa* infection, and/or an inoculum for raising antibodies. It is also understood that anti-idiotypic antibodies can be developed as vaccines based on the sequence of this invention. Such technique is described in more detail in Kennedy et al, *Vaccines* 86 "New Approaches to Immunization" Cold Spring Harbour, 1986, p. 85

Any interference with bacterial adhesion and subsequent colonization will prevent infection. Monoclonal antibodies specific for a portion of the amino acid sequence of the *P. aeruginosa* pili protein can interact with the adhesins and interfere with cell anchorage. Alternatively, a peptide or portion of the whole pilin amino acid sequence can be used as an immunogen to develop host antibodies which would, in turn, act to prevent bacterial anchorage and subsequent colonization. These methods, therefore, represent new and useful biological agents for the prevention and treatment of *P. aeruginosa* disease in humans. It should be noted that this synthetic vaccine is not directed at the dominant immunogenic or antigenic site on *P. aeruginosa* but rather to the adhesin binding site responsible for attachment of the bacterium to the surfaces of human buccal and tracheal epithelial cells. Vaccines containing effective amounts of the present polypeptides induce production of antibodies in a sufficient amount to protect the vaccinated individual from infection with *P. aeruginosa* Booster injections can be given if needed.

Thus, the word "vaccine" in its various grammatical forms is used herein in relation to the protection of a host mammal. The word "inoculum" in its various grammatical forms is used herein to describe a composition containing a polypeptide of this invention as an active ingredient used for the preparation of antibodies that immunologically bind to *P. aeruginosa* pili. A vaccine and an inoculum may thus contain the identical ingredients, but their uses are different.

The polypeptides suitable as antigens or immunogens, or both, for the present purposes can be produced synthetically or by genetic engineering techniques, and can be in monomeric as well as multimeric forms for use in vaccines, inocula, or as diagnostics. When used in a vaccine or inoculum, the polypeptide may be used alone, as in the case of an oligomer or a multimer, or used linked to another carrier moiety as a conjugate. When used alone as an immunogen, a polypeptide of this invention typically contains from about 12 to about 20 amino acid residues. Such polypeptides are preferably linked to a carrier. The polypeptides of this invention are therefore pure and homogeneous without any extraneous matter as would be experienced if the polypeptides were isolated from naturally occurring polypeptides.

Particularly useful conjugate carriers include keyhole limpet hemocyanin (KLH), tetanus toxoid, poly-L-(LYS:GLU), peanut agglutinin, poly-D-Lysine, diphtheria toxoid, ovalbumin, soybean agglutinin, bovine serum albumin (BSA), human serum albumin, and the like.

The term "manufactured" as used herein means that the polypeptide molecule or polypeptide repeating unit has been built up synthetically by chemical means, i.e., chemically synthesized or by human-mediated biological means, e.g., by genetic engineering techniques, which include recombinant DNA techniques and vaccinia viruses as vectors for vaccine antigens. Such latter technique is disclosed in more detail by Gerald Quinnan, "Proceedings of a Workshop" Nov. 13–14, 1984 Elsevier, p. 27. Thus, the manufactured polypeptides embodying the present invention are free from naturally occurring proteins and fragments thereof. The well-known solid phase chemical synthesis in which blocked amino acid residues are added in a serial manner to obtain the desired polypeptide is the preferred method of synthesis, and is discussed in greater detail herein below.

As mentioned herein above, polypeptides suitable for the purposes of the present invention can be synthesized by the well-known solid phase method. See, for example, Merrifield, *J. Am. Chem. Soc.* 85: 2149–2154 (1963), Houghten et al., *Int. J. Pept. Proc. Res.* 16: 311–320 (1980) and Parker and Hodges, J. Prot. Chem. 3: 465–478 (1985), for a complete discussion of these techniques. The solid phase method of polypeptide synthesis can be practiced utilizing a Beckman Model 990B Peptide Synthesizer, available commercially from Beckman Instruments Co., Berkeley, Calif., U.S.A.

In preparing a synthetic polypeptide of this invention by the above solid phase method, the amino acid residues are linked to a resin (solid phase) through an amide linkage from the carboxy-terminal residue.

The alpha-amino group of each added amino acid typically is protected by a tertiary-butoxy-carbonyl (t-Boc) group prior to the amino acid being added into the growing polypeptide chain. The t-Boc group is then removed prior to addition of the next amino acid to the growing polypeptide chain. Reactive amino acid side chains are also protected during synthesis of the polypeptide. Usual side-chain protecting groups used for the remaining amino acid residues are as follows: O(p-bromobenzyoxycarbonyl) for tyrosine, O-benzyl for threonine, serine, aspartic acid and glutamic acid, and S-methoxy-benzyl for cysteine, 2-chlorobenzyloxycarbonyl lysine and formyl tryptophane. Protected amino acids are recrystallized from appropriate solvents to give single spots by thin layer chromatography. Couplings are typically carried out using a 2-fold molar excess of both protected amino acid and dicyclohexyl carbodiimide over the number of milli-equivalents of initial N-terminal amino acid. For asparagine and glutamine, an equal molar amount of N-hydroxy-benzotriazole is added to the protected amino acid and dimethyl-formamide is used as the solvent. All coupling reactions are typically more than 99% complete by the picric acid test of Gisin, *Anal. Chem. Acta,* 58:248–249 (1972), or the ninhydrin test, Sarin et al., *Anal. Biochem.* 117: 147–157 (1981).

A portion of the resulting, protected, resin-bonded polypeptide (1 gram) is treated with two milliliters of anisole, and anhydrous hydrogen fluoride, 20 milliliters, is condensed into the reaction vessel at dry ice temperature. The resulting mixture is stirred at 4° for 1.0 hour to cleave the protecting groups and remove the polypeptide from the resin. After evaporating the hydrogen fluoride at a temperature of 4° C. with a stream of $N_2$, the residue is extracted with anhydrous diethyl ether three times to remove the anisole, and the residue is dried in vacuo.

The vacuum dried material is extracted with neat trifluoro acetic acid (3 times 10 milliliters each). The extraction separates the free polypeptide from the resin. After dilution with water to a concentration of 10–20% acetic acid, the resulting solution is lyophilized to provide a monomeric, unoxidized, polypeptide. The peptide released from the resin is then purified by known standard chromatographic procedures and then oxidized to give the monomeric intramolecular cyclized product.

In a typical laboratory preparation, 10 milligrams of the di-Cys polypeptide (containing amino- and carboxy-terminal cysteine residues in unoxidized form) are dissolved in 250 milliliters of 0.1 molar ammonium bicarbonate buffer having a pH value of about 8. The dissolved di-Cys poly-peptide is then air oxidized by stirring the resulting solution gently for a period of about 18 hours, or until there is no detectable free mercaptan by the Ellman test [see, Elman, Arch. Biochem. Biophys. 82:70–77 (1959)].

This cyclic oxidized peptide can also be polymerized from head-to-tail using the following procedure in which the cyclic polypeptide is dissolved in dimethylformamide (1 mg/mL) and benzotiazol- 1-yloxytris (dimethylamino) phosphonium hexafluorophosphate (1.1 molar equivalents) and diisopropylethylamine (100 μL) are added and allowed to react at room temperature for about eight hours. The polymeric peptides produced in this fashion are isolated by evaporation of the solvents and chromatographic separation. Benzyl protecting groups are then removed by treatment of the polymer with anisole and anhydrous hydrogen fluoride at −10° C. for 110 hour. After removal of the hydrogen fluoride at −10° C., with a stream of $N_2$ the residue is extracted with anhydrous diethyl ether three times to remove the anisole and the residue. Polypeptide multimers containing oxidized cyclic monomeric units may be used for the preparation of vaccine against *Pseudomonas aeruginosa.* In this event the method of synthesis must follow the known solid-phase method developed by Atherton et al., J. C. S. Perkin 1: 538–546 (1981), which disclosures are incorporated herein by reference. This method can be practiced utilizing an LKB BioLynx model 4175 peptide synthesizer available commercially from LKB Biochrom, Ltd., Cambridge, England.

In preparing a synthetic polypeptide of this invention by the above solid-phase method, the amino acid residues are linked to a resin (solid-phase) through an ester linkage from the carboxy-terminal residue.

The alpha-amino group of each added amino acid typically is protected by a 9-fluoroenyl-methoxycarbonyl (FMOC) group prior to the amino acid being added onto the growing polypeptide chain. The FMOC group is then removed prior to addition of the next amino acid to the growing polypeptide chain. Reactive amino acid side chains are also protected during synthesis of the polypeptide. Usual side-chain protecting groups used for the remaining amino acid residues are as follows: o-(p-bromobenzoyloxycarbonyl) for tyrosine, o-benzyl for threonine and serine, -phenacyl for aspartic and benzyl for glutamic acid, S-tert-butyl for cysteine and 2-chlorobenzyloxy-carbonyl for lysine. Couplings are typically carried out using a 2-fold molar excess of protected amino acid and one equivalent of dicyclohexyl carbodiimide over the number of milliequivalents of initial N-terminal amino acid. For asparagine (N) and glutamine (Q), 2 molar equivalents of N-hydroxy-benzotriazole and dicyclohexyl carbodiimide are used. All coupling reactions are typically monitored by the ninhydrin test of Sarin, *Anal. Biochem.* 117: 147–157 (1981) and are typically more than 99% complete.

A portion of this resin is cleaved to release peptide for oxidation and polymerization. Cleavage to release partially deprotected peptide is accomplished using the following method which utilized 95% trifluoroacetic acid (5 mL/50 mg resin). The resin (50 mg) is suspended in 95% trifluoroacetic acid containing anisole (3%), ethandithiol (1%) and ethylmethyl sulphide (1%) by volume and the reaction is allowed to proceed at room temperature for 2–3 hours. The resin is filtered to remove the peptide and scavengers and the resin is washed with neat trifluoroacetic acid (3–5 mL). The combined filtrates are evaporated under vacuum and the residue triturated with diethyl ether. Finally the residue is dissolved in 0.5% trifluoroacetic acid in water and lyophilized.

This crude peptide can be purified by known reversed-phase HPLC methods and the purified peptide cyclized by air oxidation in 0.1 molar ammonium bicarbonate buffer having a pH value of about 8 for a period of about 18 hours as described hereinabove. Isolation of the cyclized product from the oxidation procedure follows known chromatographic techniques. Synthesis of the polymeric polypeptide is performed by head-to-tail coupling of the free amino and carboxy-termini using benzotriazol-1-yloxytris (dimethyl amino) phosphonium hexafluorophosphate (1.1 molar equivalent) and diisopropyl ethylamine (100 1) at room temperature for about 8 hours. Purification of the multimers is then accomplished using known size-exclusion chromatographic techniques. Cleavage of the remaining benzyl side chain protecting groups is carried out by treatment of the multimers with anhydrous hydrogen fluoride (9 ml) containing anisole (1 mL) for about 1 hour at about −10° C. Isolation of the deprotected multimers is performed by evaporation of the hydrogen fluoride under a stream of $N_2$ gas while maintaining the temperature at about −10° C. The product is then triturated with diethyl ether to remove the scavenger and dissolved in aqueous 0.5% trifluoroacetic acid and lyophilized.

Alternatively, if the sequence contains benzyl protected serine and threonine in combination with tert-butyl cysteine, then cleavage before cyclization may be carried out in liquid anhydrous hydrogen fluoride (9 mL) containing anisole (1 mL) and ethandithiol (25 μL). Subsequent to this cleavage, cyclization and polymerization will provide the multimeric polypeptide. Purification at each step in the synthesis is accomplished utilizing chromatographic techniques known in the art.

Alternatively, purified cyclic polypeptide obtained by the methods described hereinabove may be attached directly to a core matrix called the multiple antigen peptide system (MAP) known in the art and described by J. P. Tam, *Proc. Natl. Acad. Sci. U.S.A.* 85: 5409–5413 (1988). Attachment of cyclic monomeric polypeptide is performed using an 8:1 molar ratio of polypeptide to core matrix in dimethylformamide containing 8 equivalents of benzotriazol-1-yloxytris (dimethylamino) phosphonium hexafluorophosphate and diisopropylethylamine (100 μL).

Vaccines and inocula of the present invention may be administered by injection, usually intramuscularly or subcutaneously, orally by means of an enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the mammal to be immunized, the carrier when used, the adjuvant when used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide.

In any event, the immunogen contained in a vaccine or an inoculum is present in an "effective amount", which amount depends upon a variety of factors as is well known in the immunological arts, e.g., the body weight of the mammal to be immunized, the carrier moiety used, the adjuvant used, the duration of protection sought, and the desired immunization protocol.

Whole antibodies, as well as substantially whole antibodies, raised to the polypeptides of this invention and antibody combining sites prepared from such antibodies constitute still another aspect of this invention. These molecules are collectively referred to as receptors.

Receptors are raised in mammals such as rabbits, goats, horses and the like by immunization using the inocula described hereinbefore. Immunization procedures are substantially the same as those used in vaccinations except that powerful adjuvants, such as Complete Freunds Adjuvant (CFA) and/or Incomplete Freunds Adjuvant (IFA) as they are commonly known, that are not acceptable for human use can be included in animal inocula.

Typical inoculum stock solutions are prepared with CFA, IFA or alum as follows: An amount of the polypeptide, synthetic polypeptide-conjugate or polymeric polypeptide sufficient to provide the desired, effective amount of polypeptide per inoculation is dissolved in PBS at a pH value of 7.2. Equal volumes of CFA or IFA are then mixed with the polypeptide solution to provide an inoculum containing polypeptide, water and adjuvant in which the water-to-oil ratio is about 1:1. The mixture is thereafter homogenized to provide the inoculum stock solution. When alum is used, about 200 micrograms of conjugate is absorbed onto about 4 milligrams of alum to prepare the stock inoculum.

Rabbits can be utilized herein to raise antipolypeptide antibodies. When so used, the host rabbit is typically injected subcutaneously with an inoculum comprising 200 micrograms of a polypeptide conjugate (polypeptide plus carrier) emulsified in CFA; 200 micrograms of polypeptide conjugate in IFA; and 200 micrograms of polypeptide conjugate with 4 milligrams alum injected intraperitoneally on days 0, 14 and 21, respectively, of the immunization schedule. Each inoculation (immunization) consists of four injections of the inoculum. Mice may be immunized in a similar way using about one tenth of the above dose per injection.

Animals are typically bled 4 and 15 weeks after the first injection. Control pre-immune serum is obtained from each animal by bleeding just before the initial immunization.

Control inoculum stock solutions can also be prepared with keyhole limpet hemocyanin (KLH), KLH in CFA or IFA, KLH-alum absorbed, KLH-alum absorbed-pertussis, edestin, thyroglobulin, tetanus toxoid, tetanus toxoid in IFA, cholera toxoid and cholera toxoid in IFA, and the like.

The efficacy of the above immunization procedure is typically determined by means of an ELISA in which the immunogenic polypeptide of this invention is used as the antigen to determine the amount of antibodies present in diluted sera obtained from the above bleeds. Sera that provide anti-polypeptide antibody titers (dilutions) of at least about 1:160 are considered useful in providing the antibodies of this invention. The typically utilized ELISA test is described in greater detail in Bittle et al., *Nature* 298, 30–33 (1982).

Suitable monoclonal receptors, typically whole antibodies, may also be prepared using hybridoma technology as described by Niman et al., *Proc. Natl. Acad. Sci. USA* 80:4949–4953 (1983). Monoclonal receptors need not only be obtained from hybridoma supernatants, but may also be obtained in generally large quantities from ascites fluid of mammals into which the desired hybridoma has been introduced. Production of monoclonal antibodies using ascites fluid is well known and will not be dealt with further herein.

A receptor of this invention binds both to the polypeptide to which it was raised and also to the corresponding pilin protein whose antigenic determinant site the polypeptide of this invention immunologically mimicks. Thus, a polypeptide of this invention may be both an immunogen and an antigen.

The receptors of this invention are a subset of the naturally occurring polyclonal antibodies since they are raised to an immunogen which mimics a small fragment of an intact pilin molecule. Consequently, receptors of this invention bind to epitopes of the polypeptide (which is a part of the pilin molecule) while naturally occurring antibodies raised to a Pseudomonas pilin bind to epitopes throughout the pilin molecule.

The polypeptides, antibodies, and antibody combining sites provided by these polypeptides, and methods of the present invention may also be used for diagnostic tests, such as immunoassays. Such diagnostic techniques include, for example, enzyme immune assay, enzyme multiplied immunoassay technique (EMIT) enzyme-linked immunosorbent assay (ELISA), radio-immune assay (RIA), fluorescence immune assay, either single or double antibody techniques, and other techniques in which either the antibody combining site or the antigen is labeled with some detectable tag. See generally Maggio, *Enzyme Immunoassay*, CRC Press, Cleveland, Ohio (1981) and Goldman, M., *Fluorescent Antibody Methods*, Academic Press, New York, N.Y. (1980).

An illustrative diagnostic system embodying the present invention to detect *P. aeruginosa* contains receptor molecules such as antibodies, substantially whole antibodies, or antibody combining sites, raised to a polypeptide of this invention. The system also includes an indicating means for signaling the presence of an immunoreaction between the receptor and the antigen. The indicating means allows the immunoreaction to be detected. When mixed with a body sample such as sputum, the receptor molecule immunoreacts with the pilin antigen to form an immunoreactant, and the indicating means present then signals the immunoreaction.

One such exemplary embodiment is an immunofluorescent assay in which a sputum smear is acetone-fixed to a plain microscope slide. An aliquot of antibodies raised in accordance with this invention, e.g., raised in rabbits, generally about 10 micrograms to about 500 micrograms, is incubated on the slides using well-known techniques.

After rinsing away an unimmunoreacted antibodies and blocking non-specific binding sites on the slide with a protein such as BSA, a second antibody, such as a goat anti-rabbit antibody can then be incubated on the test slide, if desired. The second antibody is labeled by being linked to a fluorochrome dye such as fluorscein isothiocyanate (FITC).

After this second incubation, any excess of the second antibody is rinsed off leaving any FITC-labeled goat anti-rabbit antibodies that bound to the first antibodies on the test slide. Presence of the FITC-labeled antibodies may be detected using fluorescent microscopy and thereby signal the presence of a Pseudomonas infection.

The use of whole, intact, biologically active antibodies for the receptor molecules is not necessary in many diagnostic systems such as the immunofluorescent assay described above. Rather, only the immunologically active, idiotype-containing, antigen binding and recognition receptor site; i.e., the antibody combining site, of the antibody molecule may be used. Examples of such antibody combining sites are those known in the art as Fab and F(ab')$_2$ antibody portions that are prepared by methods well known in the art.

Another diagnostic method of this invention is an ELISA assay. Here, a polypeptide antigen of this invention is bound on a solid support such as the walls of a microtiter plate. Non-specific binding sites on the microtiter well walls are thereafter blocked with a protein such as BSA. Unbound polypeptide and BSA are removed from the microtiter well as by rinsing.

A body sample such as that above is admixed with an excess of an antibody of this invention in an aqueous solution, and the admixture is maintained for a time sufficient to form an immunoreaction between the antibody and any Pseudomonas pili antigen present. That liquid admixture is then mixed with the above-described polypeptide-bound solid support to form a second admixture containing solid and liquid phases. The solid/liquid phase admixture is maintained for a time sufficient for previously unreacted antibodies to immunoreact with the polypeptide antigen. The liquid phase is thereafter separated from the solid phase. A solution of a second, labeled antibody that reacts with the first-named antibody is then admixed with the solid phase. An exemplary second antibody is an alkaline-phosphatase-linked goat anti-rabbit IgG where the first-named antibodies are raised in rabbits. The admixture formed from the solid phase and the second, labeled antibody solution is maintained for a time period sufficient to form an immunoreaction between the two antibodies. The solid and liquid phases are thereafter separated.

A solution containing a substrate for the enzyme such as p-nitrophenylphosphate is thereafter admixed with the solid phase. The optical density at a preselected wave length (e.g., 405 nanometers) may then be determined after a predetermined time period has elapsed and compared to the optical density of a control to determine whether the Pseudomonas antigen was present in the body sample.

The present invention is further illustrated by the following detailed examples.

Example 1

Polypeptide Synthesis

A series of short synthetic polypeptides whose amino acid residue sequences correspond to small segments of the Pseudomonas pilin protein were synthesized according to the method of Merrifield, J. Am. Chem. Soc. 85:2149–2154 (1963), as modified by Houghten et al., Int. J. Pept. Proc. Res. 16: 311–320 (1980), using a-Beckman Model 990B Peptide Synthesizer (Beckman Instruments Co., Berkeley, Calif., U.S.A.). The polypeptide designations and the location in the Pseudomonas pilin protein of the corresponding amino acid sequence is shown in Table 1, below.

TABLE 1

| | Synthetic Polypeptide Corresponding to Pseudomonas Pilin Segment | |
|---|---|---|
| Designation[1] | Location[2] | Amino Acid Residue Sequence |
| PAK 128-144 | 128-144 | K C T S D Q D E Q F I P K G C S |

[1]Polypeptide coupled to KLH or BSA using the benzophenone cross-linking group as described in Example 2.
[2]Location corresponds to the amino acid residue positions of the Pseudomonas pilin protein sequence described by Sastry et al., FEBS Lett. (1983) 151: 253–256.

Example 2

Polypeptide-Carrier Couplings

The peptides were conjugated to keyhole limpet hemocyanin at bovine serum albumin via a linker consisting of a norleucine spacer and a benzophenone cross-linking group (benzoyl benzoic acid), which was added to the peptide during synthesis while the peptide was still on the solid matrix. The protein (~3 mg) was first dissolved in 10 to 20 μL of water in a test tube. The protein carriers (10 mg/100 μL) were then added and mixed. Covalent attachment of the peptide to the carrier occurred following activation of the benzoylbenzoyl group by UV irradiation at 4° C. for 1 hour in a RPR 208 preparative reactor (Rayonet, The Southern New England Ultraviolet Co., Middletown, Conn.) equipped with RPR-350 mm lamps. Unconjugated haptens were removed by successive dialysis against 8M urea, 10 mM ammonium bicarbonate, and 25 mM ammonium bicarbonate. The product was freeze-dried. The peptide incorporation was determined by hydrolysis of a small sample of the conjugate and calculating the ratio of the residue norleucine with respect to any reference amino acid not found in the peptide sequence but contained in the sequence of the carrier molecule. This ratio then represents the molar ratio of peptide:carrier. Peptide/carrier ratios of about 4:1 and 10:1 were obtained for the oxidized and reduced peptides, respectively.

Example 3

Screening of Rabbit Sera for Anti-Polypeptide Antibodies

Rabbit anti-sera were screened for the presence of anti-polypeptide antibodies using an enzyme linked immunosorbent assay (ELISA). Polypeptide antigen made as described in Example 1, above, was adsorbed onto the walls of microtiter plate wells to provide solid phase bound target antigen.

A solution of conjugate (5 μg/mL) dissolved in coating buffer, sodium carbonate, pH 9.6, was used to coat the wells of a microtiter plate. The individual wells were coated with 120 μL of this solution in a humidified chamber at 4° C. for 16 hours. These plates were then washed with phosphate buffer saline/Tween three times.

Non-specific binding sites on the microtiter well walls were thereafter blocked by incubating 50 μL of 3% (w/v) BSA/PBS in each well for 4 hours at 37° C. in a humidified chamber. After incubation, excess BSA was removed by inverting and shaking the plates. Polypeptide bound to a solid support whose non-specific binding sites had been blocked was thus provided for use as target antigen.

To assay the rabbit sera for the presence of anti-polypeptide antibodies, an aliquot of each serum was serially diluted ten-fold in 1% (w/v) BSA/PBS. One hundred microliters of each dilution was contacted with solid phase bound polypeptide by a mixture in the appropriate microtiter wells prepared above. Contact was maintained by incubating the wells for about 2 hours at 37° C. in a humidified chamber, thus allowing any anti-polypeptide antibodies present in the serum dilutions to immunoreact with solid phase bound polypeptide target antigen. After incubation, the solid and liquid phases were separated by filling the wells with phosphate buffered saline/Tween inverting and shaking 3 times in seriatim.

To detect the presence of an immunoreaction between anti-polypeptide antibodies and solid-phase antigen, 100 μL of a 1:1000 dilution of goat anti-rabbit IgG labelled with alkaline phosphatase (Boehringer-Mannheim Biochemicals, Indianapolis, Ind.) in phosphate buffered saline/Tween, was added to each well and incubated for about 2 hours in a humidified chamber at room temperature. The wells were washed three times with phosphate buffered saline/Tween in seriatim. A substrate solution (50 μL) containing 1 mg of p-nitrophenylphosphate in 1 mL of 10% diethanolamine, pH 9.8, was added to each well and the reaction was allowed to continue for about 45 to 60 min. at room temperature. The amount of indicating reaction (color development) was quantitated by measuring the absorbance of each well at 405 nm. Rabbit antisera demonstrating an absorbance which was 0.05 units above background were determined and the results are tabulated in Table 2.

TABLE 2

| End Point Titers - Direct Elisa Using Rabbit Antisera Against Peptide Conjugate | |
|---|---|
| Designation[1] | Peptide-Conjugate Titer |
| 17-R1 | $3.5 \times 10^{-6}$ |
| 17-R2 | $7.1 \times 10^{-6}$ |
| 17-01 | $4.5 \times 10^{-6}$ |
| 17-02 | $2.1 \times 10^{-6}$ |

[1]Antisera derived from 4 different rabbits.

Example 4

Screening of Rabbit Sera for Anti-Pilin Antibodies

Rabbit antisera were screened for binding to Pseudomonas pili isolated from two strains, PAK and PAO, using direct enzyme-linked immunoabsorbent assay (ELISA). The pili were isolated and purified as described by Paranchych et al., *Can. J. Microbiol.* (1979) 25: 1175–1181 and described in Example 5. A 5 μg/mL solution of pili dissolved in coating buffer sodium carbonate, pH 9.6, was used to coat the wells of a microtiter plate. The individual wells were coated with 120 μL of this solution in a humidified chamber at 4° C. for 16 hours. These plates were then washed with phosphate buffered saline/Tween three times.

Non-specific binding sites on the microtiter well walls were thereafter blocked by incubating 50 μL of 3% (w/v) BSA/PBS in each well for 4 hours at 37° C. in a humidified chamber. After incubation, excess BSA was removed by inverting and shaking the plates. Polypeptide bound to a solid support whose non-specific binding sites had been blocked was thus provided for use as target antigen.

To assay the rabbit sera for the presence of anti-polypeptide antibodies, an aliquot of each serum was serially diluted 10-fold in 1% (w/v) BSA/PBS. One hundred microliters of each dilution was contacted with solid phase bound polypeptide by a mixture in the appropriate microtiter wells prepared above. Contact was maintained by incubating the wells for about 2 hours at 37° C. in a humidified chamber, thus allowing any anti-polypeptide antibodies present in the serum dilutions to immunoreact with solid phase bound polypeptide target antigen. After incubation, the solid and liquid phases were separated by filling the wells with phosphate buffered saline/Tween, inverting and shaking 3 times in seriatim.

To detect the presence of an immunoreaction between anti- antibodies and solid-phase antigen, 100 μL, of a 1:1000 dilution of goat anti-rabbit IgG labelled with alkaline phosphatase (Boehringer-Mannheim Biochemicals, Indianapolis, Ind.) in phosphate buffered saline/Tween, was added to each well and incubated for about 2 hours in a humidified chamber at room temperature. The wells were washed three times with phosphate buffered saline/Tween in seriatim. A substrate solution (50 μL) containing 1 mg of p-nitrophenylphosphate in 1 mL of 10% diethanolamine, pH 9.8, was added to each well and the reaction was allowed to continue for about 45 to 60 min at room temperature. The amount of indicating reaction (color development) was quantitated by measuring the absorbance of each well at 405 nm. Rabbit antisera demonstrating an absorbance which was 0.05 units above background were determined and the results are tabulated in Table 3.

TABLE 3

End Point Titers ( SD) (n = 3) - Direct
ELISA Using Rabbit Antisera Against
Pili from Strains PAK and PAO

| Designation[1] | Pill Titer | |
|---|---|---|
| | PAK | PAO |
| 17-R1 | $1.0 \times 10^{-5}$ | $4.15 \times 10^{-4}$ |
| | $(1.2 \times 10^{-5})$ | $(3.7 \times 10^{-4})$ |
| 17-R2 | $1.6 \times 10^{-5}$ | $4.5 \times 10^{-4}$ |
| | $(0.4 \times 10^{-5})$ | $(0.3 \times 10^{-4})$ |
| 17-01 | $1.5 \times 10^{-5}$ | $2.0 \times 10^{-5}$ |
| | $(0.7 \times 10^{-5})$ | $(0.8 \times 10^{-5})$ |
| 17-02 | $2.0 \times 10^{-5}$ | $1.3 \times 10^{-4}$ |
| | $(1.2 \times 10^{-5})$ | $(1.6 \times 10^{-4})$ |

[1] Antisera derived from 4 different rabbits.
2 The endpoint (n = 3) was determined as the cutoff at an A405 of 0.05 AU.

Example 5

Purification of Pili

The purification procedure used was previously described by Paranchych et al., *Can. J. Microbiol.* (1979) 25: 1175–1181. Bacteria were grown on solid medium in large pans as described above and then harvested by scraping the surface of the agar and suspending the cells from 36 trays (about 100 g wet weight) in 1000 mL SSC buffer. The cells were then stirred with a magnetic stirrer at 5° C. for 2 h. Large bits of agar were removed by passing the suspension through a sieve and the pili were removed from the cells by blending in 200 mL portions for 2 min at 2000 rpm with a Sorvall Omnimixer. After removing bacteria by centrifugation at 10,000×g for 15 min. the NaCl concentration of the supernatant solution was adjusted to 0.5M. Polyethylene glycol 6000 (PEG 6000) was then added to a final concentration of 1% w/v, and the solution was allowed to sit for 18 h at 4° C. Both pili and flagella precipitated under these conditions and were removed by centrifugation at 7000×g for 20 min. To remove flagella, the pellet was resuspended in a 10% w/v $(NH_4)_2SO_4$ solution (pH 4.0) and allowed to stand at 4° C. for 2 h. Pili precipitated under these conditions while flagella remained in suspension. Remaining flagella were removed by repeating the ammonium sulfate precipitation step. The final pellet was redissolved in water, dialyzed exhaustively to remove $(NH_4)_2SO_4$, then subjected to CsCl density gradient centrifugation. The latter procedure involved layering 20 mL of pili solution onto 16 mL of a preformed step gradient in which the CsCl density ranged from 1.1 to 1.5. After 20 h of centrifugation at 20,000 rpm in an SW27 rotor using a Beckman L2-65B ultracentrifuge, the pilus band (buoyant density of about 1.3 g/cm$^3$) was removed, then subjected to a second CsCl density gradient centrifugation step. After removing the pilus band from the second CsCl gradient and dialyzing to remove CsCl, the pili were resuspended in distilled water and washed by repeated centrifugation for 2 h at 50,000 rpm in a 60-Ti fixed-angle rotor. The pili were judged pure when SDS polyacrylamide gel electrophoretic examination of the preparation showed a single protein band of heavily overloaded samples (100 μg pilin per sample).

Example 6

Western Blot Assay

The rabbit antisera were further screened to determine their ability to immunoreact with Pseudomonas pilin protein in a Western blot assay. Pseudomonas pilin protein was isolated from strains PAK and PAO as described in Example 5. Sodium dodecyl sulfate-polyacrylamide gel electrophoresis was carried out according to the Laemmli method by using 15% polyacrylamide running gels. Purified pili (5 μg) and whole-cell lysate (3×10$^7$ bacteria) were used. The whole-cell lysate was prepared by boiling the PAK cells for 2 to 3 min in 100 μL of sample buffer (2.5% sodium dodecyl sulfate in 0.25M Tris, pH 6.8) used to dissolve proteins to be loaded onto the sodium dodecyl sulfate-polyacrylamide gel. The mixture was then centrifuged on a bench-top Microfuge; 10 μL of the supernatant was removed and diluted with 15 μL of sample buffer before being loaded onto the gel. After separation, the proteins were transblotted at 0.2 A for 2 to 6 h onto nitrocellulose paper according to the method of Towbin et al., *P.N.A.S.* (*USA*) (1979) 76:4350–4354. Excess protein-binding capacity of the nitrocellulose sheet was blocked with 5% gelatin solution (59 gelatin in 100 mL Tris buffered saline, 20 mM Tris, 500 mM NaCl, pH 7.5) for 1 hour at room temperature. The nitrocellulose sheet was then washed twice with 0.05% Tween-20 in Tris buffered saline. The sheet was then treated with antipeptide antisera (1:250) diluted with 1% gelatin in Tris buffered saline containing Tween-20 at room temperature for 16 hours. Excess sera was removed by washing twice with Tris buffered saline containing Tween-20. The pilin bands were detected with an immunoassay kit (BioRad Laboratories, Richmond, Calif.) by using a goat anti-rabbit IgG alkaline phosphatase conjugate diluted 3000-fold with 1% gelatin in Tris buffered saline containing Tween-20. Incubation with this conjugate was carried out at room temperature for 1 hour. Excess conjugate was removed from the sheet by two washes with Tris buffered saline containing Tween-20 followed by one wash with Tris buffered saline alone. Immunoreactants were detected using p-Nitro blue Tetrazolium chloride in the presence of 5-Bromo-4-chloro-3-indolyl phosphate toluidine salt. Immunoreactants appear as purple red bands. The results are shown in Table 4.

TABLE 4

Results of Immunoblot Analysis of PAK and
PAO Pilin Proteins with Peptide-Conjugate
Rabbit Antisera

| Designation[1] | Pilin | |
|---|---|---|
| | PAK | PAO |
| 17-R1 | +++[2] | + |
| 17-R2 | +++ | + |
| 17-01 | +++ | ++ |
| 17-02 | +++ | + |

[1] Antisera derived from 4 different rabbits.
[2] +++, intense band; ++, moderately intense band; +, weak band.

Example 7

Buccal Epithelial Cell Preparation

BEC's were collected from ten healthy non-smoking male volunteers via wooden application sticks rubbed gently on the inside of cheeks, three wooden application sticks per cheek. These sticks were rubbed gently together in 30 mL phosphate buffered saline to suspend the BEC's. These cells were washed three times with 30 mL phosphate buffered saline by successive centrifugation (650×g spins) and resuspended. The final pellet was suspended in 5 mL of 10 mm phosphate buffered saline at pH 7.2. This suspension was filtered (prewetted 70 μm nylon mesh) and the cells were diluted to a final concentration of $2 \times 10^5$ cells/mL in phosphate buffered saline at pH 7.2. This suspension is stored at 4° C. until ready for use.

Example 8

Tracheal Epithelial Cell Preparation

Human ciliated tracheal epithelial cells (TECs) were obtained from patients in the Surgical Intensive care unit at Toronto General Hospital by bronchoscopic brushing of the bronchial mucosa as described by Franklin et al., *Infection and Immunity* (1987) 55, 23-1525.

TECs were obtained by bronchoscopy from surgical patients (under general anesthetic), intubated intensive care unit (ICU) patients, and health volunteers. For the surgical and ICU patients, bronchoscopy was performed with a flexible Olympus Type 2 BF bronchoscope inserted through an endotracheal tube. A cytology brush was used to abrade the tracheal-bronchial mucosa, and TECs were collected in high-glucose Dulbecco modified Eagle medium containing 1% sodium citrate.

The cell suspension obtained by bronchoscopy contained both ciliated and nonciliated cuboidal and columnar epithelial cells in addition to various amounts of mucus, erythrocytes, granulocytes, and cell debris and was not suitable for direct use in an adhesion assay. The cell suspension was vortexed briefly, sequentially passed through 70- and 30-μm-pore-size-mesh nylon screens, washed twice ($500 \times g$ for 15 min at 4° C.) with 10 l of 0.01M phosphate-buffered saline (pH 7.2) (PBS), and then resuspended in 1 ml of PBS. The cell suspension was then fractionated by density gradient centrifugation ($500 \times g$ for 15 min at 4° C. in a swinging bucket rotor) on a PBS-preformed ($48,000 \times g$ for 40 min at 4° C.) 65% (vol/vol) percoll gradient. The TEC band was collected and applied to a second percoll gradient. The ciliated TEC band was collected from the second gradient, and the cells were washed once in PBS and then resuspended in 1.5 ml of PBS. A direct cell count was performed with a hemacytometer; cell viability was determined by trypan blue dye exclusion. The cell fractionation procedure typically yielded ($2.08 \pm 0.34$) $\times 10^5$ cells (mean±standard error), of which $32.8 \pm 6.5\%$ were ciliated TECs. The vast majority of these cells were viable, and in many cases the cilia were still beating. The fractionated TECs contained only epithelial cells, were essentially free of contaminating mucus, and were used directly for adhesion assays.

Example 9

Pak 128-144 Binding to BECs

An immunoassay was performed to assess the binding of PAK 128-144 red and PAK 128-144 ox to BECs. BECs (0.2 ml at $2.0 \times 10^5$ BECs/ml) were added to an equal volume of synthetic peptide (0 nmol/ml to 120 nmol/ml) in PBS and incubated at 37° C. and agitated at 300 rpm. After 1 h, BECs were collected by centrifugation (13,000 $\times g$ for 2 min at room temperature) and washed 5 times with PBS. Monoclonal antibody PK99H (0.2 ml of a $10^{-3}$ dilution in PBS of purified IgG with a titre of $10^6$) was added to the BEC pellet and incubated as described above for 1 h. The BECs were then collected by centrifugation (13,000 $\times g$ for 2 min at room temperature) and washed 5 times with PBS. Goat anti-mouse IgG (H+L) immunoglobin G-horseradish peroxidase conjugate (Jackson Laboratories) was added to the BEC pellet (0.2 ml of a 1:10000 dilution in PBS) and the mixture incubated as described above for 1 h. The BECs were collected by centrifugation (13,000 $\times g$ for 2 min at room temperature) and washed 5 times with PBS. The pellet was resuspended in 0.2 ml of 1 mM ABTS (2,2'-azino-di-(3-ethylbenzthiazoline sulfonic acid)) in 10 mm citrate buffer pH $4.2 + 0.03\%$ peroxide and transferred to a clean tube. The horseradish peroxidase enzyme reaction was stopped by the addition of 0.2 ml of 4 mM $NaN_3$ and the optical density at 405 nm was determined after removal of the BECs by centrifugation. The BEC concentration in each tube was determined with a hemocytometer at the end of the assay prior to the removal of BECs by centrifugation. Results are shown in FIG. 1 wherein binding of synthetic peptide Ac17red (■) and synthetic peptide Ac17ox (+) to human BECs is plotted. Binding of the synthetic peptides to BECs was determined by a whole cell ELISA assay utilizing the monoclonal antibody PK99H (which binds to both Ac17px and Ac17red) to quantitate the amount of synthetic peptide bound to the surface of BECs.

Example 10

Pak 128-144 Inhibition of Pilus Binding to BECs

Figure 2:
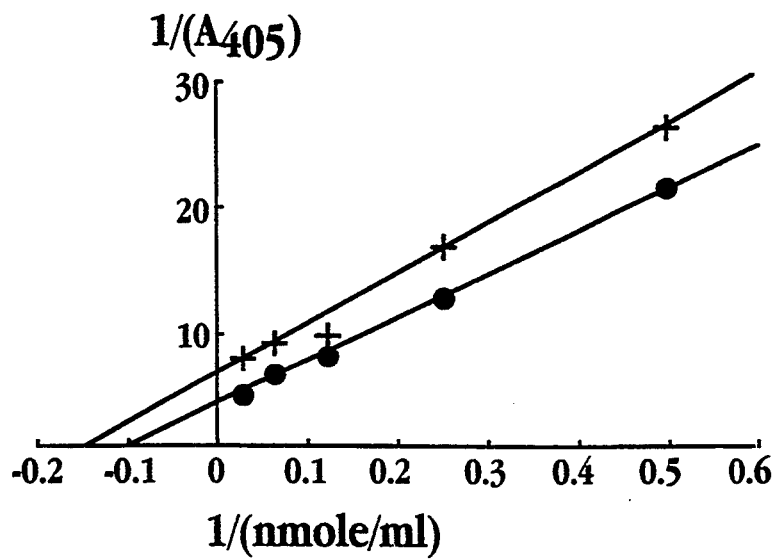
FIG. 2 is a modified Lineweaver-Burk plot of the binding of synthetic peptides to human BECs.
Figure 3:
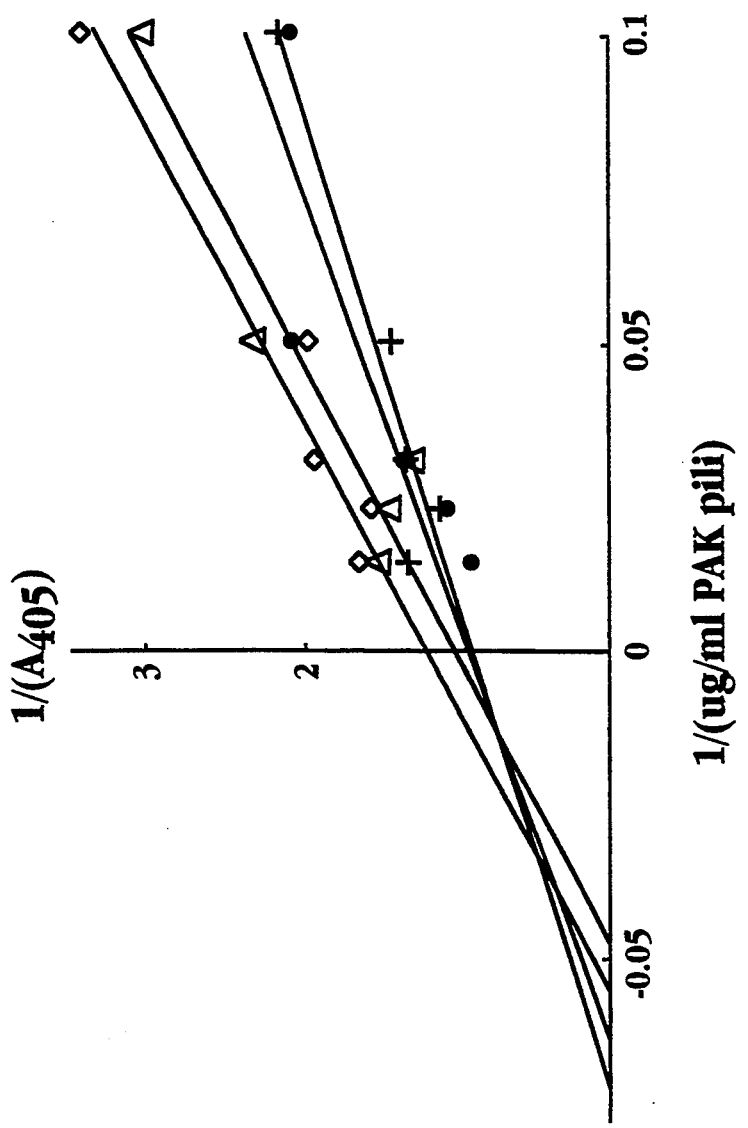
FIG. 3 is a modified Lineweaver-Burk plot of the binding of PAK pili to human BECs.
Figure 4A:
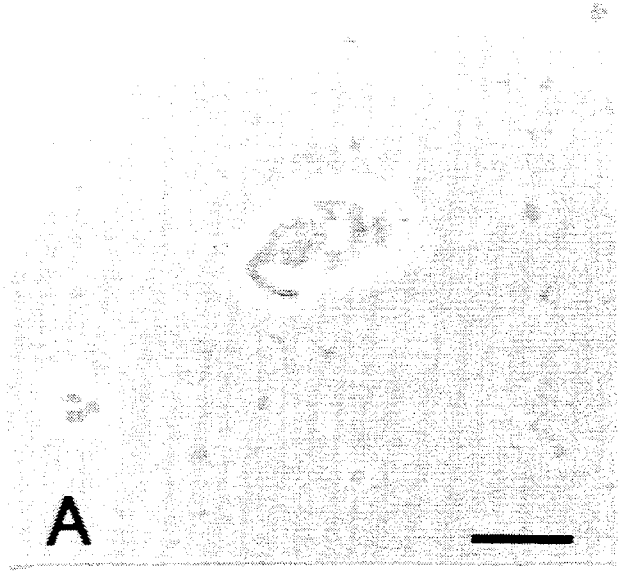
FIG. 4a-4d show micrographs A, B, C and D of indirect immunofluorescent localization of PAK pili binding to fractionated ciliated TECs.
Figure 4B:
Figure 4C:
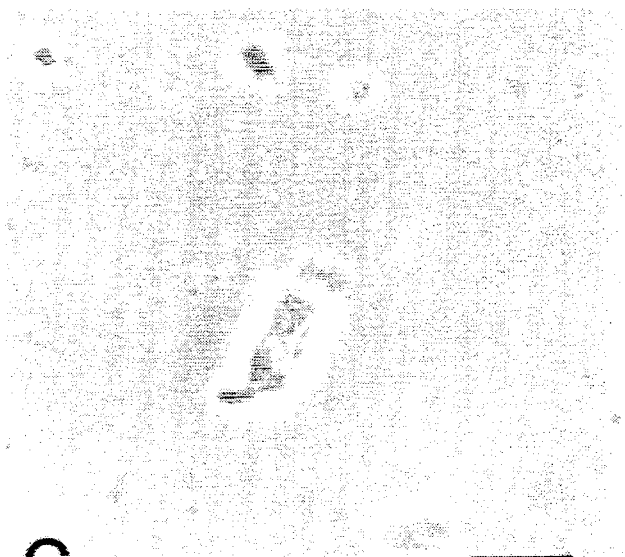
Figure 4D:
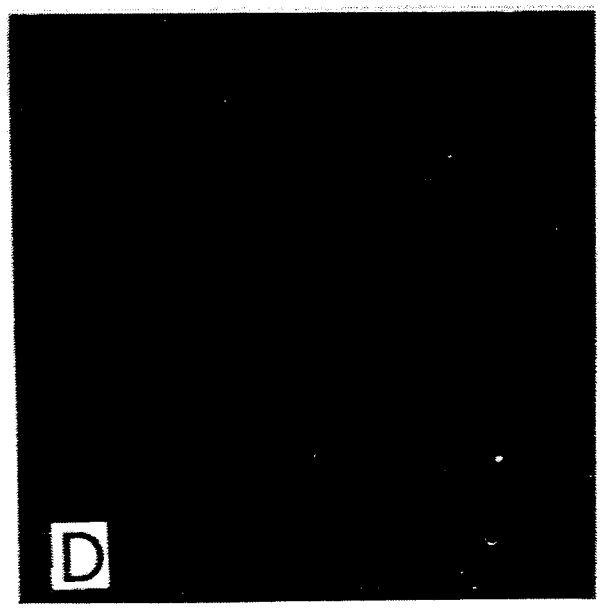

An immunoassay was performed to assess the effect of PAK 128-144 red on pilus binding to BECs. BECs (0.2 ml at $2.0 \times 10^5$ BEC/ml) and synthetic peptide PAK 28-144 red (0.1 ml such that a final concentration of 0,40,80 or 120 nmol/ml of synthetic peptide was obtained) were preincubated for 30 min at room temperature. Pili (0.1 ml of 0 μg/ml to 100 μg/ml) were then added to the BECs with varying concentrations of synthetic peptide (0,40,80 for 120 nmol/ml). The mixtures were then incubated for 2 h at 37° C. while being agitated at 300 rpm. BECs and bound pili were then collected by centrifugation (13,000 $\times g$ for 2 min) and washed 5 times with PBS to remove unbound pili. Monoclonal antibody PK3B (0.1 ml of a $10^{-4}$ dilution in PBS) (this antibody recognizes PAK pili, but does not react with synthetic peptide PAK 128-144) was then added to the BECs with bound pili and incubated for 1 h as described above. The remainder of the immunoassay was the same as described for pilus binding to BECs. Results are shown in FIG. 2 wherein a modified Lineweaver-Burk plot of the binding of synthetic peptides Ac17red (■) and Ac17ox (+) to human BECs is plotted, and in FIG. 3, wherein a modified Lineweaver-Burk plot of the binding of PAK pili to human BECs in the presence of 0 (X), 40 ($\overline{X}$), 80 (Δ), and 120 (◊) nmoles/ml of synthetic peptide Ac17red are plotted.

Example 11

Pili and Pak 128-144 Binding to TECs

Figure 5A:
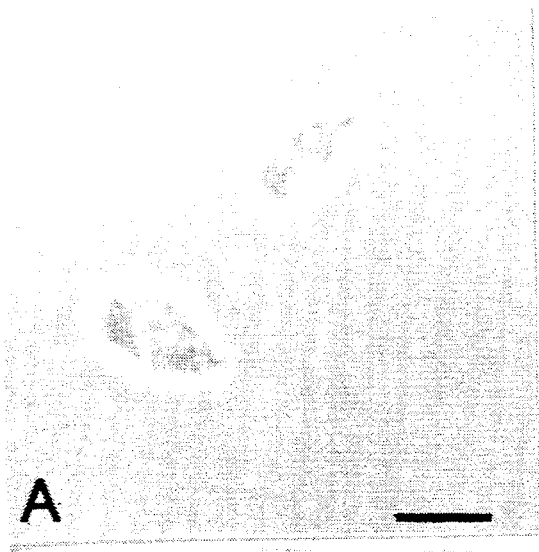
Figure 5B:
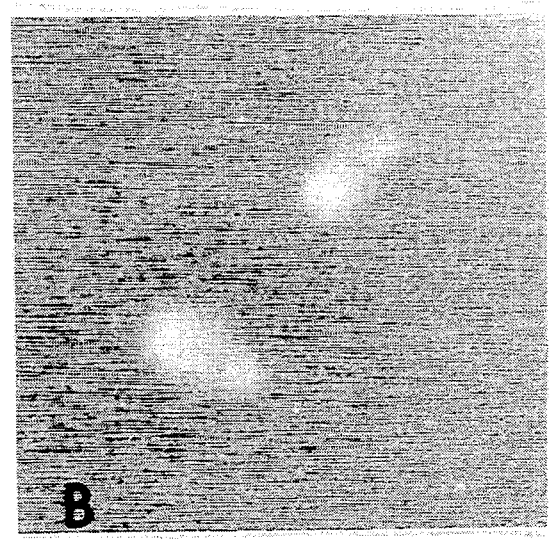
Figure 5C:
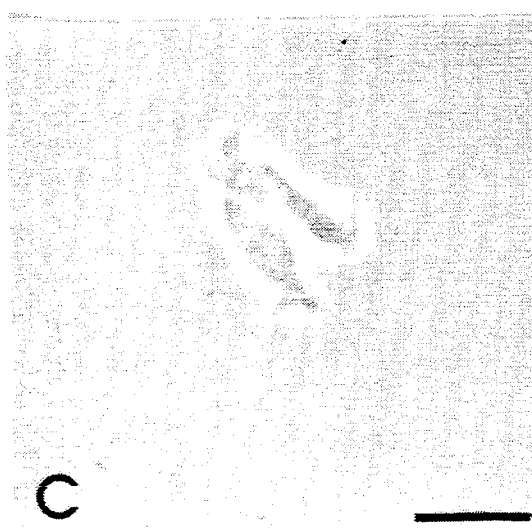

TECs (0.1 ml of $1 \times 10^5$ cells/ml) were mixed with an equal volume of PAK pili (345 g/ml), PAK 128-144 red (10 nmol/ml), PAK 128-144 ox (50 nmol/ml) or PBS. The mixture was incubated at 37° C. for 1 h and agitated at 300 rpm. TECs were then collected by centrifugation (6,000 $\times g$ for 1 min at room temperature) and washed 3 times with PBS. Anti-pilus monoclonal antibodies PK3B (0.1 ml of a $10^{-4}$ dilution of purified IgG with a titre of $10^8$ in PBS) or monoclonal antibody PK99H (0.1 ml of a $10^{-3}$ dilution of Purified IgG with a titre of $10^6$ in PBS) were added to TECs incubated with pili or synthetic peptides PAK 128-144 red and PAK 128-144 ox, respectively (PK3B reacts with PAK pili without affecting pilus binding activity, but PK3B does not react with either PAK 128-144 red or PAK 128-144 ox). Control preparations included monoclonal antibodies PK3B and PK99H incubated TECs in PBS without the presence of pili and synthetic peptides. TECs were then collected by centrifugation and washed 3 times with PBS. Rabbit anti-mouse IgG, IgM (H+L) affinity purified IgG conjugated to fluorescein isothiocyanate (Cedarlane laboratories) in PBS (0.1 ml of a 1/100 dilution) was added to the washed TECs preparations and incubated for 30 min at 37° C. and agitated at 300 rpm. The TECs were washed 3 times as described above and resuspended in 0.1 ml of PBS. Wet mounts were prepared, and examined by epifluorescence and phase contrast microscopy using a Lietz Laborlux equipped with a MPS4 camera system. Photographs were recorded with Kodak T-Max film. Results are shown in FIG. 4 wherein indirect immunoflourescent localization of PAK pili binding to fractionated ciliated TECs A) phase contrast micrograph of TEC with bound PAK pili; B) immunoflourescent micrograph of PAK pili bound primarily to the cilia and luminal portion of the cytoplasmic membrane of the same ciliated TECs visualized by phase contrast microscopy in A, C and D are the phase contrast image and the immunoflourescent image of a control TEC exposed to monoclonal antibody PK3B and FITC conjugated anti-mouse but not exposed to PAK pili. Further results are shown in FIG. 5, wherein indirect immunoflourescent localization of binding of synthetic peptides Ac17ox (A and B) and Ac17red (C and d) to human ciliated TECs. Micrographs E and F are control preparations not exposed to the synthetic peptides but exposed to monoclonal antibody PK99H and FITC conjugated anti-mouse IgG. FIGS. A, C and E are phase contrast micrographs of the same cells visualized by immunoflourescence microscopy in FIGS. B, D and F. Note that synthetic peptide Ac17ox and Ac17red both bind primarily to the cilia and the luminal portion of the cytoplasmic membrane of TECs. The apparent limited binding of Ac17ox to the TECs is due to the lesser affinity of monoclonal antibody PK99H for oxidized form of the peptide relative to the reduced form of the peptide.

Example 12

Pak 128-144 Binding to BEC Blots

The discontinuous sodium dodecyl sulfate polyacrylamide gel electrophoresis (SDS-PAGE) described by Laemmli and Favre, J. Mol. Biol. (1973) 80:575-599 was employed. SDS-PAGE of BECs was performed as described above using 8% acrylamide gels. BECs ($2 \times 10^5$ cells/ml) were solubilized at 100° C. for 15 min in 2% (wt/vol.) SDS, 5% (vol/vol) β-mercaptoethanol, 10% (vol/vol) glycerol in 0.625 mM Tris buffer pH 6.8. Solubilized BECs (25 μl) were loaded on the gel and electrophoresed at 20 mA/gel (constant current). Electrophoretically separated material was transferred to nitrocellulose (Schleicher & Schuell) by electrophoretic transfer as described by Towbin et al., P.N.A.S. (U.S.A.) (1979) 76: 4350-4354. After transfer nitrocellulose blots were blocked with 3% (wt/vol) BSA, 0.25% (wt/vol) gelatin, 0.1% (vol/vol) normal rabbit serum, 0.05% (vol/vol) Nonidet P-40, 5 mM EDTA, 150 mM sodium chloride in 50 mM Tris buffer pH 7.5 at 37° C. for at least 3 h.

Figure 6:
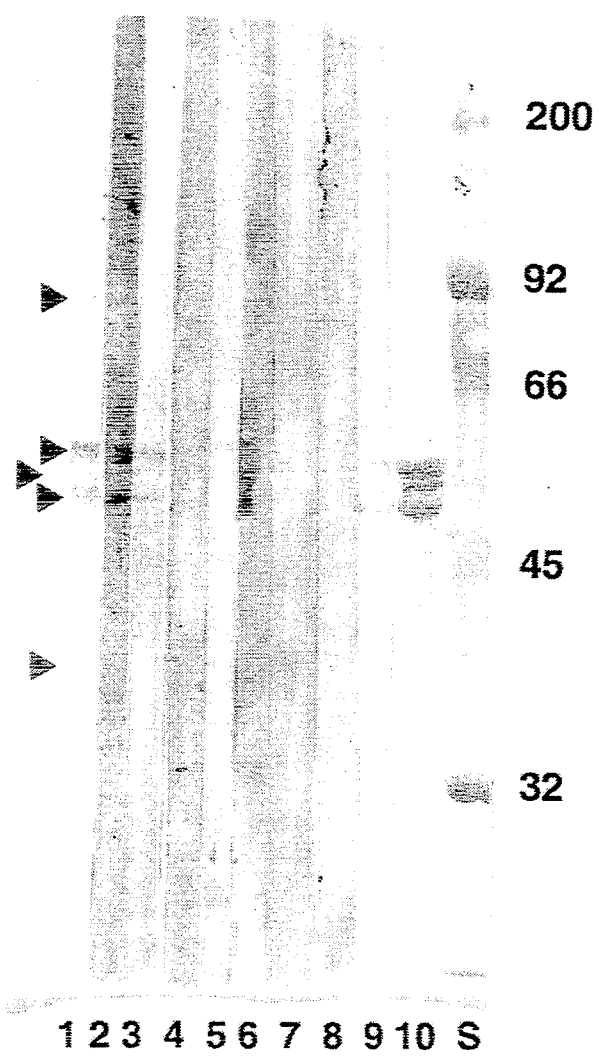
FIG. 6 is a blot showing the binding of PAK pili and synthetic peptide to blotted BEC proteins on nitrocellulose.

Before use blots were rinsed with PBS. Blots were then incubated with PAK 128-144red (0 to 20 nmol/ml) at 37° C. shaking at 100 rpm. After 2 h, blots were washed 3 times with BBBB (TTBS) (10 min per wash). Murine monoclonal antibody PK99H ($10^{-4}$ dilution in TTBS) (this monoclonal antibody recognizes the PAK 128-144 synthetic peptide) was incubated with the blot at 37° C. for 1 h at 100 rpm. The blot was then washed 3 times with TTBS. A goat anti-mouse IgG (H+L) immunoglobin-alkaline phosphatase conjugate (Jackson Laboratories) in TTBS was added and incubated for 1 h as above. The blot was washed 3 times with TTBS and once with Tris buffered saline. A substrate solution (NBT/BCIP) consisting of 0.33 mg/ml nitro blue tetrazolium chloride, 0.165 mg/ml 5-bromo-4-chloro-3-indolyl-phosphate, 100 mM sodium chloride, 5 mM magnesium chloride in 100 mM Tris buffer pH 9.5 was added and color development stopped by rinsing the blot in distilled water. Results are shown in FIG. 6, wherein binding of PAK pili and synthetic peptide Ac17red to blotted BEC proteins on nitrocellulose is plotted. Binding of synthetic peptide to the immobolized proteins was assessed (following blocking of the nitrocellulose with BSA) utilizing monoclonal antibody PK99H (or monoclonal antibody PK3B for PAK pili) followed by standard immunoblotting methods. PAK pili at 150 μg/ml (lane 1), Ac17red at 20 (lane 2), 10 (lane 3), 5 (lane 4), or 0 (lane 5) nmoles/ml was incubated with the blotted BEC protein. BEC proteins oxidized by exposure to 30 mM periodate and then reduced with borohydride before incubation with 20 nmoles/ml of Ac17red (lane 6) or buffer (lane 7). Ac17red at 20 nmoles/ml was initially reacted with 100 μg/ml of Fab fragments of monoclonal antibody PK99H (which binds to synthetic peptide Ac17red) (lane 8) or reacted with 100 μg/ml of Fab fragments of monoclonal antibody PK41C which does not bind to synthetic peptide Ac17red (lane 9). Amido black stained BEC proteins (lane 10). Standard molecular weight markers stained with amido black (lane S).

Example 13

Periodate Oxidation of BEC Blots

Periodate oxidation (30 mM periodate) and subsequent potassium borohydride reduction of BEC blots was performed as described by Woodward et al., J. Immunol. Meth., 78: 143-153 (1985). One or two cycles of oxidation-reduction were done on preblocked blots. Blots were assessed for synthetic peptide binding as described above in Example 12. Results are also shown in FIG. 6.

Example 14

Inhibition of Pilus Binding to BECs

An equal volume of Fab fragments of affinity purified IgG specific for the various synthetic peptide-BSA conjugates in PBS (0.1 ml at 0.3-0.61 mg/ml) was added to purified PAK pili (0.1 ml at 100 ug/ml) and incubated at room temperature for 30 min. To this BECs (0.2 ml at $2.0 \times 10^5$ BECs/ml) were added and the mixture incubated at 37° C., shaking at 300 rpm in a New Brunswick gyroshaker. After 2 h, BECs were collected by centrifugation (13 000 Xg for 2 min) and washed 5 times with PBS. Monoclonal antibody PK3B (0.2 ml of a 10-4 dilution in PBS) was added to the BEC pellet and incubated as described above for 1 h. The BECs were then collected by centrifugation and washed 5 times with PBS. Goat anti-mouse IgG Fc-specific immunoglobin G-peroxidase conjugate (Jackson Laboratories) was added to the mixture incubated as described above for 30 min. The BECs were collected by centrifugation and washed 5 times with PBS. The pellet was resuspended in 0.2 ml of ABTS (2,2'-azino-di-(3ethylbenzthiazoline sulfonic acid)) in citrate buffer pH 4.2+0.03% peroxide and transferred to a clean tube. The reaction was stopped by the addition of 0.2 ml of 4 mM NaN3 and the optical density at 405 nm was determined after removal of the BECs by centrifugation. The BEC concentration in each tube was determined with a hemocytometer at the end of the assay prior to the removal of BECs by centrifugation.

TABLE 5

Results of Inhibition Studies:
FAB Fragments Produced from Polyclonal
Antisera Raised in Rabbits to the
Synthetic Peptide 128-144 from PAK Pilin Sequence

| | Protein Conc (mg/ml)[2] | % of Control | S.D.[3] | Abs 405 nm[1] | S.D. |
|---|---|---|---|---|---|
| 128-144 r1 | 0.43 | 72.03 | 4.89 | 0.547 | 0.034 |
| 128-144 r2 | 0.55 | 62.30 | 0.13 | 0.473 | 0.001 |
| 128-144 o1 | 0.45 | 70.62 | 2.53 | 0.563 | 0.018 |
| 128-144 o2 | 0.61 | 35.68 | 7.60 | 0.271 | 0.053 |
| Preimmune | 0.30 | 100.00 | 13.91 | 0.759 | 0.098 |
| PK99H | 0.05 | 64.62 | 2.47 | 0.490 | 0.017 |
| Control | 0.00 | 92.66 | 11.33 | 0.703 | 0.080 |

End point titration by ELISA of all Fabs at all concentrations shows was approximately $10^3$
[1]Corrected for background.
[2]Protein measured by Folin-Lowry using BSA as standard.
[3]Experiments were done in triplicate and whole experiments were replicated 3 times.

Example 15

Preparation of Fab Fragments

Fab fragments were prepared using immobilized papain (Pierce). Briefly, affinity purified antibody was dialyzed against 20 mM cysteine HCl, 10 mM tetrasodium ethylenediaminetetraacetic acid (EDTA) in 20 mM sodium phosphate buffer pH 6.2. Antibody (1 ml containing approximately 2 mg antibody) was added to 0.5 ml immobilized papain and incubated at 37° C. for 20 h with shaking at 150 rpm. The immobilized papain was removed by centrifugation and the supernatant containing the Fab fragments diluted with 1 ml of PBS. The Fab fragments were purified by HPLC using a protein G column eluted with PBS. Fab fragments were collected in the flow through, while Fc fragments were eluted from the column with 10 mM glycine pH 2.75. Fab fragments were concentrated by placing the Fab effluent in dialysis tubing (molecular weight cutoff of <8000) and extracting liquid from the dialysis sack using polyethylene glycol (molecular weight of 15,000-20,000). The fragments were then dialyzed against PBS. Activity of Fab fragments was checked by ELISA and production of FAB fragments confirmed by SDS-PAGE.

Example 16

Effect of Fab Fragments to the Synthetic Peptide Conjugates Corresponding to Amino Acid Sequences of Pak Pilin on Pak Pili Binding To Human Buccal Cells (BECs)

Figure 7:
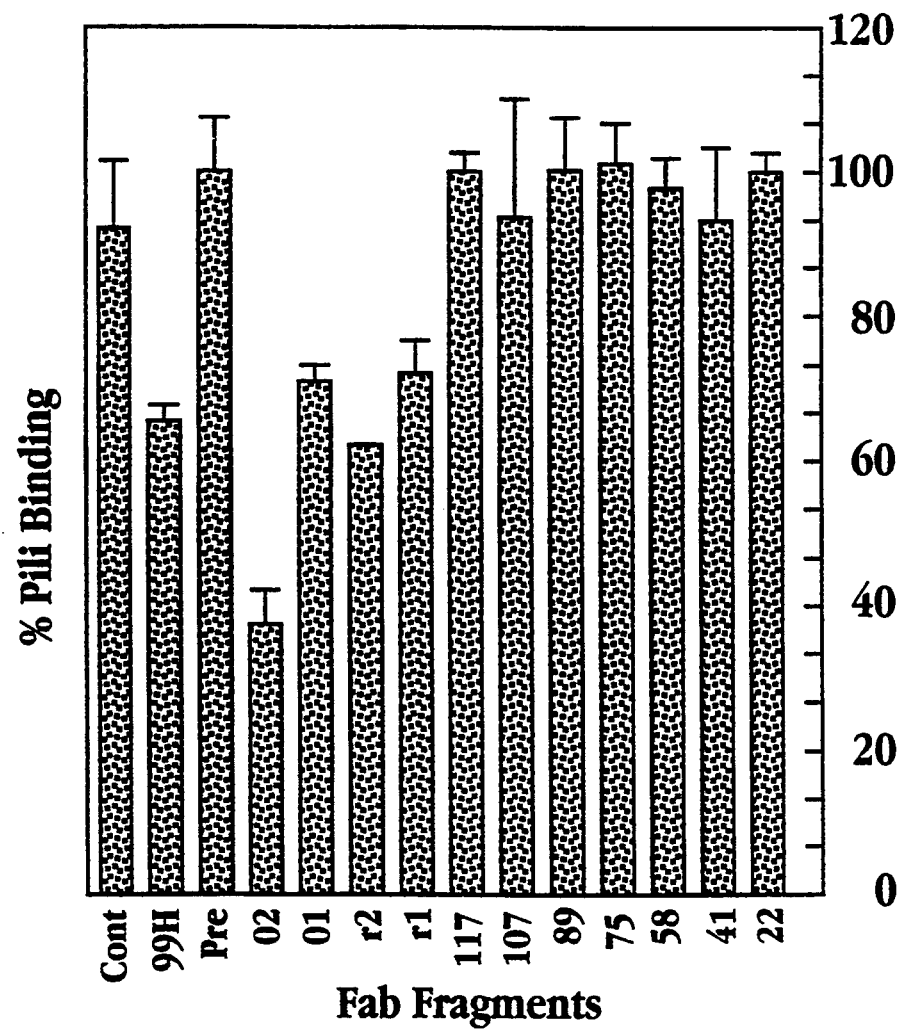
FIG. 7 is a bar graph demonstrating the Fab fragments produced against regions other than the C-terminal of PAK pilin and are ineffective in preventing pilin binding to BECs.

Fab fragments were preincubated with pili before the addition of BECs (1 × 10[5] cells/mL final concentration) and pili binding was detected using monoclonal antibody PK3B. All Fabs were diluted such that their final titre as measured by ELISA to PAK pili was 10[3]. The results are shown in the bar graph of FIG. 7. the bar graph demonstrates that Fab fragments produced against regions other than the C-terminal of PAK pilin are ineffective at preventing pilin binding to BECs. The most effective fragments are r1, r2, 01 and 02, directed at residues 128-144, which reduce pilin binding to 40% to 70% of the control and preimmune serum. This is similar to the effect shown by Fab 99H which is made from anti-PAK pilin monoclonal antibody PK99H which is also directed at this C-terminal region. This graph helps to demonstrate that the C-terminal loop region, residues 128-144, are specifically involved in pilin binding to BECs. The legend applicable to FIG. 7 is as folows: 22=Fab fragments produced against residues 22-33,41=Fab fragments produced against residues 41-49, 58=Fab fragments produced against residues 58-70, 75=Fab fragments produced against residues 75-84, 89=Fab fragments produced against residues 89-99, 107=Fab fragments produced against residues 107-116, 117=Fab fragments produced against residues 117-125, r1=Fab fragments produced against residues 128-144 with cysteine residues in the reduced state, r2=Fab fragments produced against residues 128-144 with cysteine residues in the reduced states, o1-Fab fragments produced against residues 128-144 with cysteine residues in the oxidized state, o2=Fab fragments produced against residues 128-144 with cysteine residues in thebxidized state, Pre=Fab fragments produced from the preimmune sera, 99H=Fab fragments produced from anti-PAK pilin monoclonal antibody PK99H, Cont=No Fab fragments added.

Although preferred embodiments of the invention are described herein in detail, it will be understood by those skilled in the art that variations may be made thereto without departing from the spirit of the invention or the scope of the appended claims.

We claim:

1. A method of producing immunity in a mammalian subject against infection by *Pseudomonas aeruginosa*, comprising
   vaccinating the subject with an immunogenically active peptide composition composed of
   (A) a pilin peptide consisting of amino acid residues 128-144 of a Pseudomonas pilin protein, including one of the sequences:
      (i) C T S D Q D E Q F I P K G C,
      (ii) C K S T Q D P M F T P K G C,
      (iii) C T S T Q E E M F I P K G C,
      (iv) C A T T V D A K F R P N G C,
      (v) C T S N A D N K Y L P K T C,
   where the two cysteine residues (C) in the peptide are crosslinked;
   (B) an immunogenic carrier to which the peptide is attached; and
   (C) a pharmaceutically acceptable diluent.

2. The method of claim 1, wherein said peptide consists of amino acid residues 128-144 of PAK pilin protein, and includes the sequence C T S D Q D E Q F I P K G C.

* * * * *